(12) United States Patent
Ragini et al.

(10) Patent No.: US 7,776,458 B2
(45) Date of Patent: Aug. 17, 2010

(54) SILYL-SUBSTITUTED CYCLOMETALATED TRANSITION METAL COMPLEX AND ORGANIC ELECTROLUMINESCENCE DEVICE USING THE SAME

(75) Inventors: Das Rupasree Ragini, Suwon-si (KR); Hee-Kyung Kim, Anyang-si (KR); Young-Hun Byun, Yongin-si (KR); Lyong-Sun Pu, Suwon-si (KR); O-Hyun Kwon, Seoul (KR); Young-Mok Son, Hwaseong-si (KR); Jong-Jin Park, Guri-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 491 days.

(21) Appl. No.: 11/398,612

(22) Filed: Apr. 6, 2006

(65) Prior Publication Data

US 2006/0228582 A1    Oct. 12, 2006

(30) Foreign Application Priority Data

Apr. 12, 2005  (KR) ...................... 10-2005-0030288

(51) Int. Cl.
*H01L 51/54* (2006.01)
*C09K 11/06* (2006.01)

(52) U.S. Cl. ...................... 428/690; 428/917; 313/504; 313/506; 257/40; 257/E51.044; 252/301.16; 546/4; 546/14

(58) Field of Classification Search ................. 428/690, 428/917; 313/504, 506; 257/40, E51.044; 546/4, 14

See application file for complete search history.

(56) References Cited

U.S. PATENT DOCUMENTS

| | | | |
|---|---|---|---|
| 5,484,922 A * | 1/1996 | Moore et al. ................. 546/7 |
| 2002/0064681 A1 | 5/2002 | Takiguchi et al. |
| 2002/0134984 A1* | 9/2002 | Igarashi ..................... 257/79 |
| 2004/0121184 A1* | 6/2004 | Thompson et al. ......... 428/690 |
| 2004/0124766 A1* | 7/2004 | Nakagawa et al. ......... 313/504 |

FOREIGN PATENT DOCUMENTS

WO    WO 02/15645 A1    2/2002

\* cited by examiner

*Primary Examiner*—D. Lawrence Tarazano
*Assistant Examiner*—Michael Wilson
(74) *Attorney, Agent, or Firm*—Robert E. Bushnell, Esq.

(57) ABSTRACT

Silyl-substituted cyclometalated transition metal complexes have good thermal stability and enabling highly efficient phospholuminescence and an organic electroluminescent device may use the Silyl-substituted cyclometalated transition metal complexes. The transition metal complexes, which are suitably used for forming an organic layer of the organic electroluminescent device, can emit light in the wavelength range of 400-650 nm, and induce white electroluminescence when combined with green or red luminescent materials.

17 Claims, 7 Drawing Sheets

SILYL-SUBSTITUTED CYCLOMETALATED TRANSITION METAL COMPLEX AND ORGANIC ELECTROLUMINESCENCE DEVICE USING THE SAME

CROSS-REFERENCE TO RELATED PATENT APPLICATION AND CLAIM OF PRIORITY

This application claims the benefit of Korean Patent Application No. 10-2005-0030288, filed on Apr. 12, 2005, in the Korean Intellectual Property Office, the disclosure of which is incorporated herein in its entirety by reference.

BACKGROUND OF THE INVENTION

1. Field of the Invention

The present invention relates to a silyl-substituted cyclometalated transition metal complex and an organic electroluminescence device using the same, and more particularly, to a silyl-substituted cyclometalated transition metal complex capable of emitting light over a wide range from a blue region to a red region from the triplet metal-to-ligand charge transfer (MLCT) state and having good thermal stability and an organic electroluminescence device using the same as an organic layer forming material.

2. Description of the Related Art

Generally, an organic electroluminescent (hereinafter referred to as EL) device is a spontaneous light-emitting display device which emits light by the energy generated through the recombination of electrons and holes when an electric field is applied to thin films made of fluorescent or phosphorescent organic compounds (hereinafter referred to as organic layers), and provides various advantages suitable to be used for portable electronic devices, including lightness, constructional simplicity, high quality, wide viewing angle, high color purity, perfect implementation of motion pictures, low power consumption, a low driving voltage, and so on.

A general organic EL device includes an anode, a hole transport layer, an emission layer, an electron transport layer, and a cathode, sequentially formed on a substrate. The hole transport layer, the emission layer, and the electron transport layer are organic layers made of organic compounds. The organic EL device having the above-described configuration is driven as follows. When a voltage is applied between the anode and the cathode, holes injected from the anode migrate to the emission layer via the hole transport layer. Electrons emitted from the cathode are injected into the emission layer via the electron transport layer. The electrons and the holes recombine in the emission layer to generate excitons. While the excitons radioactively decay, light corresponding to a band gap of the molecules is emitted.

Materials forming the emission layer of the organic EL device are classified into a fluorescent material that uses singlet excitons and a phosphorescent material that uses triplet excitons, according to a light-emitting mechanism. The fluorescent material or the phosphorescent material forms an emission layer by itself or by being doped into an appropriate host material. As a result of the electron excitation, singlet excitons and triplet excitons are produced in the host. Statistically, the singlet excitons and the triplet excitons in an organic EL device are created in a ratio of about 1:3.

Organic EL devices using a fluorescent material as a material for forming an emission layer are disadvantageous in that triplets are consumed from the host. However, organic EL devices using a phosphorescent material as a material for forming an emission layer are advantageous in that singlet excitons and triplet excitons are both utilized to achieve the internal quantum efficiency of 100%. Thus, an organic EL device using a phosphorescent material as a material for forming an emission layer has a high luminescence efficiency compared with an organic EL device using a fluorescent material.

Introduction of a heavy metal such as Ir, Pt, Rh, or Pd to organic molecules has led to spin-orbital coupling due to a heavy atom effect so that a triplet state and a singlet state coexist, enabling a forbidden transition, thereby allowing phospholuminescence to occur even at room temperature.

More recently, developments have led to the discovery of highly efficient green and red luminescent materials using photoelectroluminescence of up to 100%.

As highly efficient luminescent materials using phospholuminescence, various materials employing various transition metal compounds containing a transition metal such as iridium or platinum, have been being reported. However, materials satisfying requirements for realizing a full-color display of high efficiency or white electroluminescence at low power consumption are only restricted to ones emitting in the green and red ranges, and enough blue phosphorescent materials have not been reported, which is becoming a barrier to the development of phospholuminescent full-color display devices.

To address the above-described problems, intensive development of blue emission materials is under way (International Patent Publication No. WO 02/15645 A1, U.S. Patent Publication No. 2002/0064681 A1). Also, there have been proposed organometallic complexes having a bulky functional group or a functional group having a high intensity ligand field, e.g., a cyano group, introduced thereto to increase a difference between HOMO-LUMO energy levels by transforming the molecular geometry (Mat. Res. Soc. Symp. Proc. 708, 119, 2002; 3rd Chitose International Forum on Photonics Science and Technology, Chitose, Japan, 6-8 Oct., 2002).

In addition, a cyclometalated transition metal complex composed of nitrogen atoms and carbon atoms and an organic EL device including the same are disclosed in U.S. Patent Publication No. 2002/0134984 A1. However, all of these materials do not show satisfactory physical properties in color purity, luminescence efficiency, lifespan, thermal stability, etc.

SUMMARY OF THE INVENTION

The present invention provides a silyl-substituted cyclometalated transition metal complex capable of emitting light over a wide wavelength range from a blue region to a red region from the triplet metal-to-ligand charge transfer (MLCT) and having good thermal stability.

The present invention also provides an organic EL device capable of emitting light over a wide wavelength range from a blue region to a red region and having good heat stability.

According to an aspect of the present invention, there is provided a silyl-substituted cyclometalated transition metal complex represented by Formula 1:

[Formula 1]

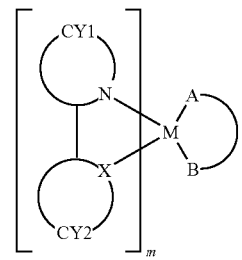

(1)

in which M is a transition metal; X is C, S, O, or N; CY1 and CY2 are each an aromatic or aliphatic ring; A^B is a monoanionic bidentate chelating ligand; at least one of CY1, CY2, and A^B has a silyl group represented by Formula $SiR^1R^2R^3$, in which $R^1$, $R^2$, and $R^3$ are each independently alkyl, aryl, alkyloxy, or aryloxy; and m is 1 or 2.

In Formula 1, the

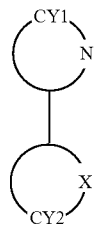

the CY2 may be a group selected from the group consisting of:

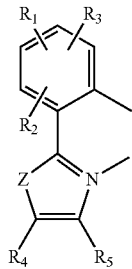 (2)

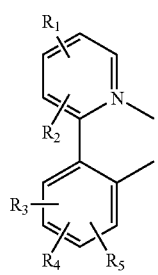 (3)

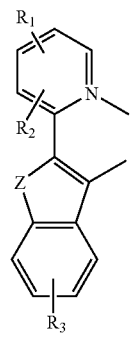 (4)

-continued

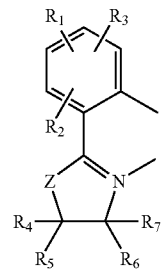 (5)

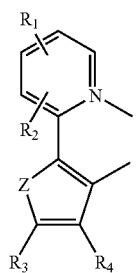 (6)

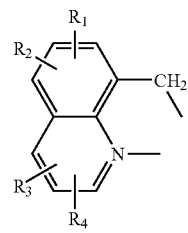 (7)

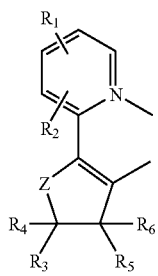 (8)

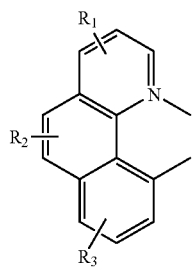 (9)

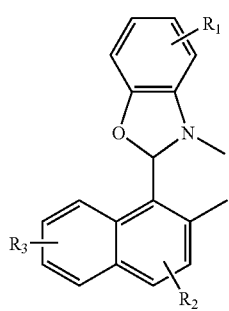 (10)
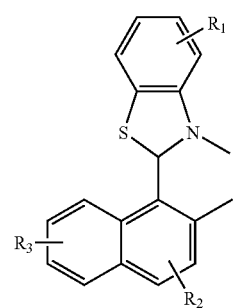 (11)
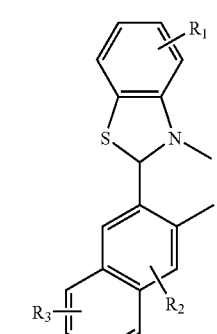 (12)
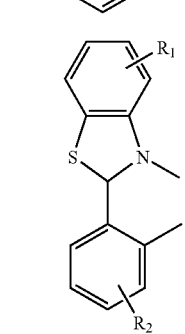 (13)
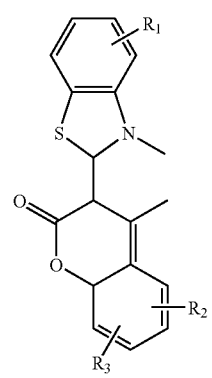 (14)
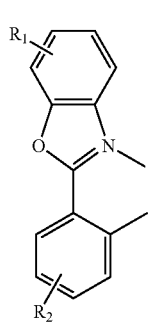 (15)
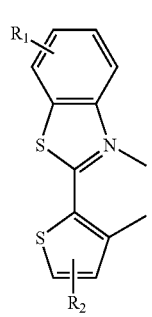 (16)
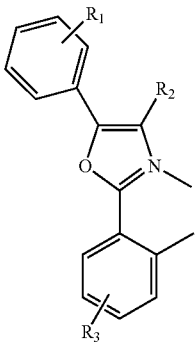 (17)
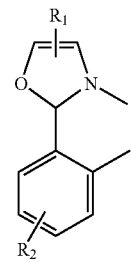 (18)
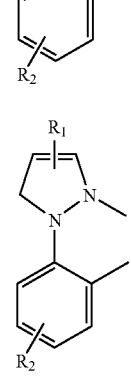 (19)

-continued

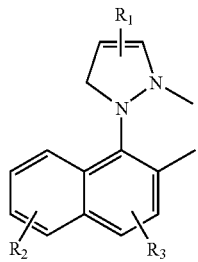
(20)

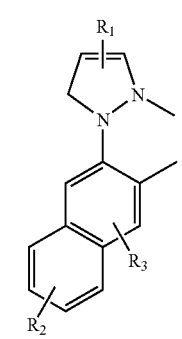
(21)

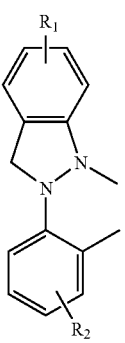
(22)

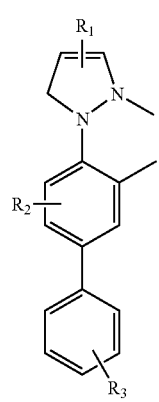
(23)

in which Z is S, O, or $NR_8$; and $R_1$, $R_2$, $R_3$, $R_4$, $R_5$, $R_6$, $R_7$, and $R_8$ are each independently selected from hydrogen, halogen, CN, silyl, alkyl, aryl, arylene, alkoxy, aryloxy, amino, and $CF_3$.

In Formula 1, the A^B may be selected from:

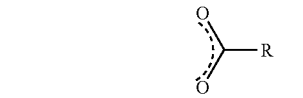
(24)

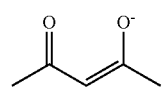
(25)

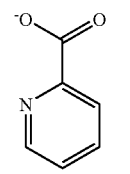
(26)

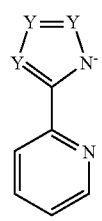
(27)

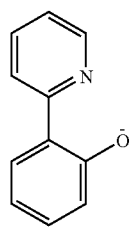
(28)

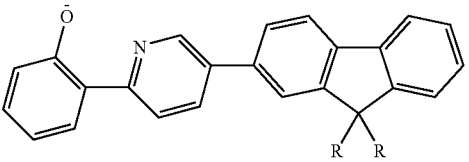
(29)

in which Y is C, S, O, or N; and R is alkyl, arylalkyl, alkoxy, or aryloxy, in which each ring of arylalkyl or aryloxy may be substituted with halogen, $CF_3$, CN, silyl, alkyl, aryl, alkoxy, aryloxy, amino, or arylene.

Each of the ligands may be substituted with halogen, $CF_3$, CN, silyl, alkyl, aryl, alkoxy, aryloxy, amino, or arylene.

According to another aspect of the present invention, there is provided an organic electroluminescent device including an organic layer between a pair of electrodes, wherein the organic layer includes the silyl-substituted cyclometalated transition metal complex represented by Formula 1.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
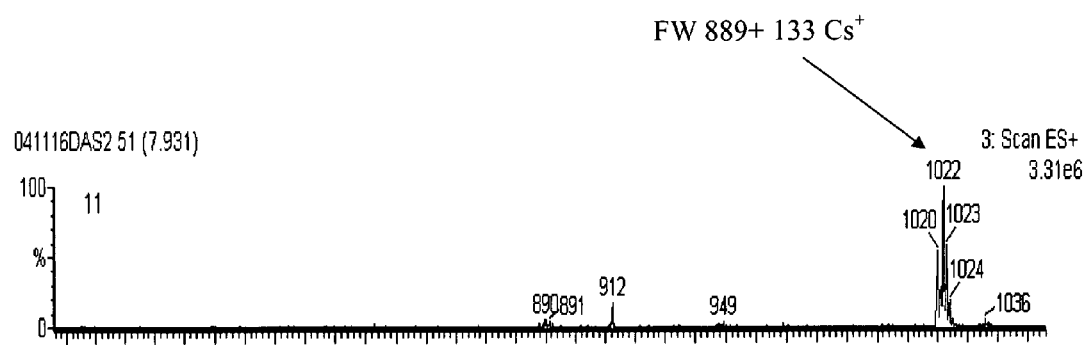
FIGS. 1A and 1B are the mass spectra of the compounds prepared in the Examples 1 and 2 of the present invention.

Reference will now be made in detail to the present preferred embodiments of the present invention.

A silyl-substituted cyclometalated transition metal complex according to an embodiment of the present invention has a substituted silyl group on at least one of a major ligand and an auxiliary ligand to have heat stability and enable highly efficient blue luminescence.

The silyl-substituted cyclometalated transition metal complex according to an embodiment of the present invention is represented by Formula 1:

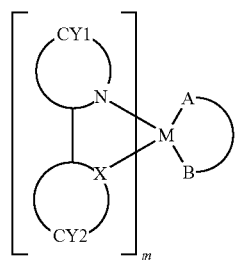

(1)

in which M is a transition metal; X is C, S, O, or N; CY1 and CY2 are each an aromatic or aliphatic ring; A^B is a monoanionic bidentate chelating ligand; at least one of CY1, CY2, and A^B has a silyl group represented by Formula $SiR^1R^2R^3$, in which $R^1$, $R^2$, and $R^3$ are each independently alkyl, aryl, alkyloxy, or aryloxy; and m is 1 or 2.

The cyclometalated transition metal complex represented by Formula 1 has a silyl group substituted on at least one of ligands coordinated to a metal. Due to the presence of the silyl group, the efficiency of an EL device is significantly increased and heat stability thereof is also increased.

In Formula 1, the

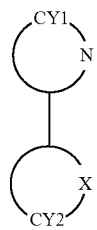

has N and X which bind to M, and may be selected from:

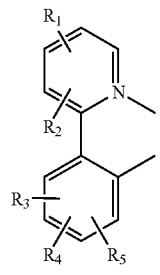
(2)

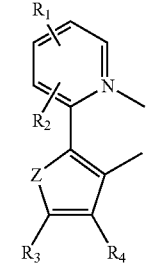
(3)

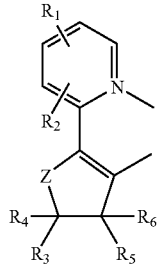
(4)

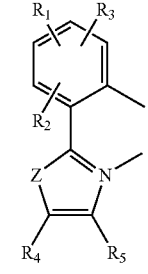
(5)

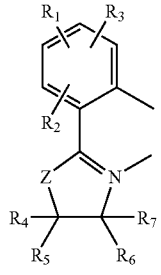
(6)

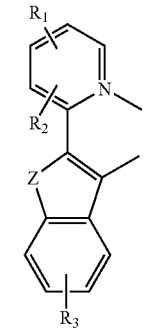
(7)

-continued
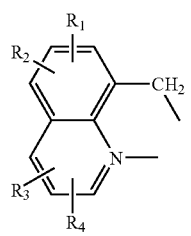
(8)
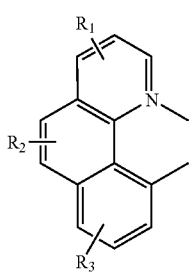
(9)
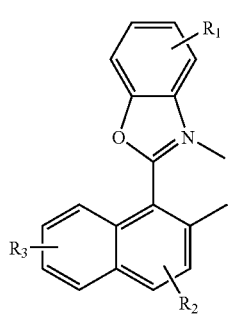
(10)
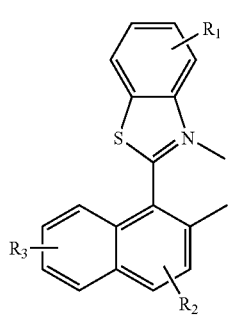
(11)
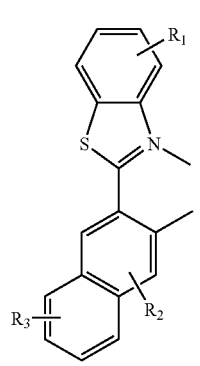
(12)
-continued
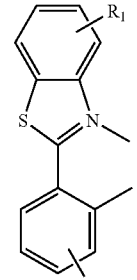
(13)
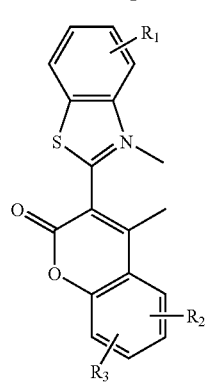
(14)
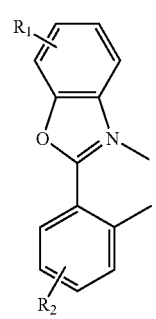
(15)
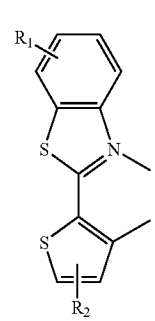
(16)
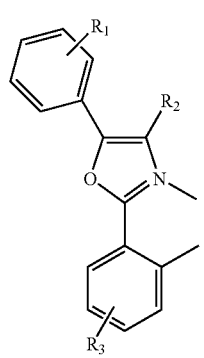
(17)

(18) 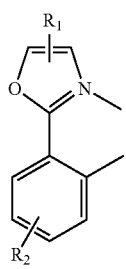
(19) 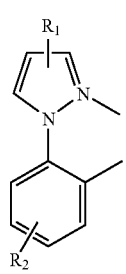
(20) 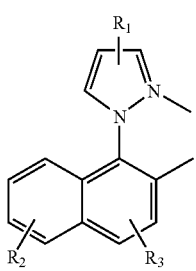
(21) 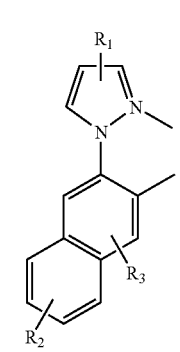
(22) 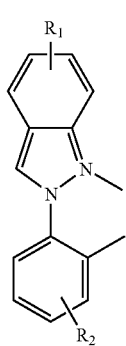
(23) 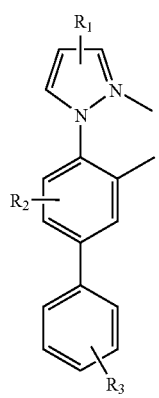
in which Z is S, O, or $NR_8$; and $R_1, R_2, R_3, R_4, R_5, R_6, R_7$, and $R_8$ are each independently selected from hydrogen, halogen, CN, silyl, alkyl, aryl, arylene, alkoxy, aryloxy, amino, and $CF_3$.
In Formula 1, the
(hereinafter referred to as A^B) may be selected from:
(24) 
(25) 
(26) 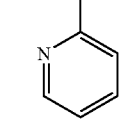
(27) 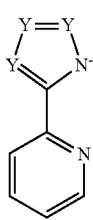

-continued

(28)
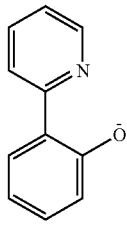

(29)
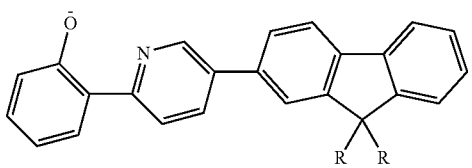

in which Y is C, S, O, or N; and R is alkyl, arylalkyl, alkoxy, or aryloxy, in which each ring of arylalkyl or aryloxy may be substituted with halogen, $CF_3$, CN, silyl, alkyl, aryl, alkoxy, aryloxy, amino, or arylene.

Each of the ligands may be substituted with halogen, $CF_3$, CN, silyl, alkyl, aryl, alkoxy, aryloxy, amino, or arylene.

Specific examples of the silyl-substituted cyclometalated transition metal complex represented by Formula 1 include the following compounds:

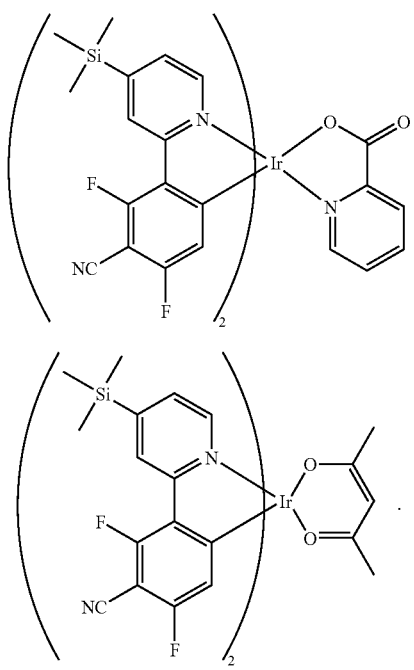

In Formula 1, the transition metal M may be Ru, Rh, Os, Ir, Pt, or Au, and most preferably, Ir.

The compound represented by Formula 1 according to an embodiment of the present invention provides a maximum emission in the wavelength range of 400-650 nm.

The silyl-substituted cyclometalated transition metal complex represented by Formula 1 can be prepared by the method in which a $[Ir((CY1)-(CY2))_2Cl]_2$ derivative is used as a starting material for providing the cyclometalating moiety, as reported by Watts group. See F. O. Garces, R. J. Watts, Inorg. Chem. 1988, (35), 2450, which is incorporated herein by reference.

The synthesis routes of a transition metal complex having an acetylacetonate ligand according to an embodiment of the present invention will now be described.

Referring to Reaction Scheme 1, the $[Ir((CY1)-(CY2))_2Cl]_2$ derivative having a silyl group substituted on CY1 and 2,4-pentanedione were reacted in a mixture of tetrahydrofuran and methyl alcohol (4:1) solvents at 50° C. for 8 hours, giving the silyl-substituted cyclometalated transition metal complex.

[Reaction Scheme 1]

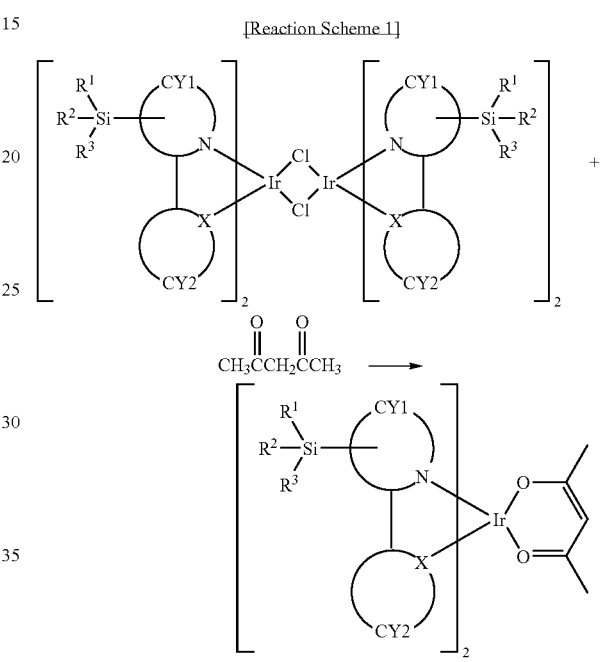

in which X, $R^1$, $R^2$, $R^3$, CY1, and CY2 are as defined in Formula 1.

The organic electroluminescent device according to the present invention is manufactured by forming an organic layer, particularly an emission layer, using the cyclometalated transition metal complex represented by formula 1. The transition metal complex represented by formula 1 is very advantageously used as a phospholuminescent dopant material, which is a material for forming the emission layer, and exhibits excellent emission characteristics in the blue range.

When the transition metal complex represented by formula 1 is used as a phospholuminescent dopant, the organic layer may further comprises at least one selected from the group consisting of at least one high molecular weight host, a mixture of a high molecular weight host and a low molecular weight host, a low molecular weight host, and non-luminous high molecular weight matrix. As the high molecular weight host, the low molecular weight host and the non-luminous high molecular weight matrix, any useful materials known in the art as materials for forming an emission layer of an organic electroluminescent device can be used. Examples of the high molecular weight host include, but are not limited to, poly(vinylcarbazole) (PVK), polyfluorene and the like, examples of the low molecular weight host include, but are not limited to, CBP(4,4'-N,N'-dicarbazole-biphenyl), 4,4'-bis [9-(3,6-biphenylcarbazollyl)]-1,1'-biphenyl, 9,10-bis[(2',7'- t-butyl-9',9'-spirobifluorenylanthracene, tetrafluorene and the like. Examples of the non-luminous high molecular weight matrix include, but are not limited to, polymethylmethacrylate, polystyrene, polycarbonate and the like.

Preferably, the transition metal complex represented by formula 1 is contained in an amount of about 1 to 30 parts by weight based on 100 parts by weight of the emission layer forming material. Examples of methods useful to introduce the transition metal complex to the emission layer include vacuum deposition, sputtering, printing, coating, ink-jet printing, electron-beam application, and so on.

The transition metal complex represented by formula 1 can induce white electroluminescence when combined with green or red luminescent materials.

The thickness of the organic layer is preferably in a range of 30 to 100 nm. The term "organic layer" used herein refers to a layer made of an organic compound formed between a pair of electrodes in an organic electroluminescent device, for example, an emission layer, an electron transport layer, a hole transport layer, and the like. The organic electroluminescent device may have a structure selected from the group consisting of anode/emission layer/cathode, anode/buffer layer/emission layer/cathode, anode/hole transport layer/emission layer/cathode, anode/buffer layer/hole transport layer/emission layer/cathode, anode/buffer layer/hole transport layer/emission layer/electron transport layer/cathode, and anode/buffer layer/hole transport layer/emission layer/hole blocking layer/cathode, but is not particularly limited to these structures.

The buffer layer may be composed of any materials commonly used in the art, and preferred are copper phthalocyanine, polythiophene, polyaniline, polyacetylene, polypyrrole, polyphenylene vinylene, and derivatives thereof but not limited thereto.

The hole transport layer may be composed of any materials commonly used in the art, and preferred is polytriphenylamine but not limited thereto.

The electron transport layer may be composed of any materials commonly used in the art, and preferred is polyoxadiazole but not limited thereto.

The hole blocking layer may be composed of any materials commonly used in the art, and preferred are TAZ, BCP, TBAP, LiF, $BaF_2$ or $MgF_2$ but not limited thereto.

The organic electroluminescence device according to the present invention can be manufactured in accordance with the conventional apparatus and methods in the art without any limitations.

The silyl-substituted cyclometalated transition metal complex can emit light of wavelengths in a range from 400 to 650 nm. Light emitting diodes (LEDs) using such organometallic complexes can be used in applications such as light sources for a full color display, backlighting, signboards, optical communication, indoor decoration, and the like.

Hereinafter, the present invention will now be described in more detail with reference to the following Examples. However, these examples are given for the purpose of illustration and not of limitation.

Reference Example 1

Synthesis of $[(F_2CNpTMSpy)_2IrCl]_2$

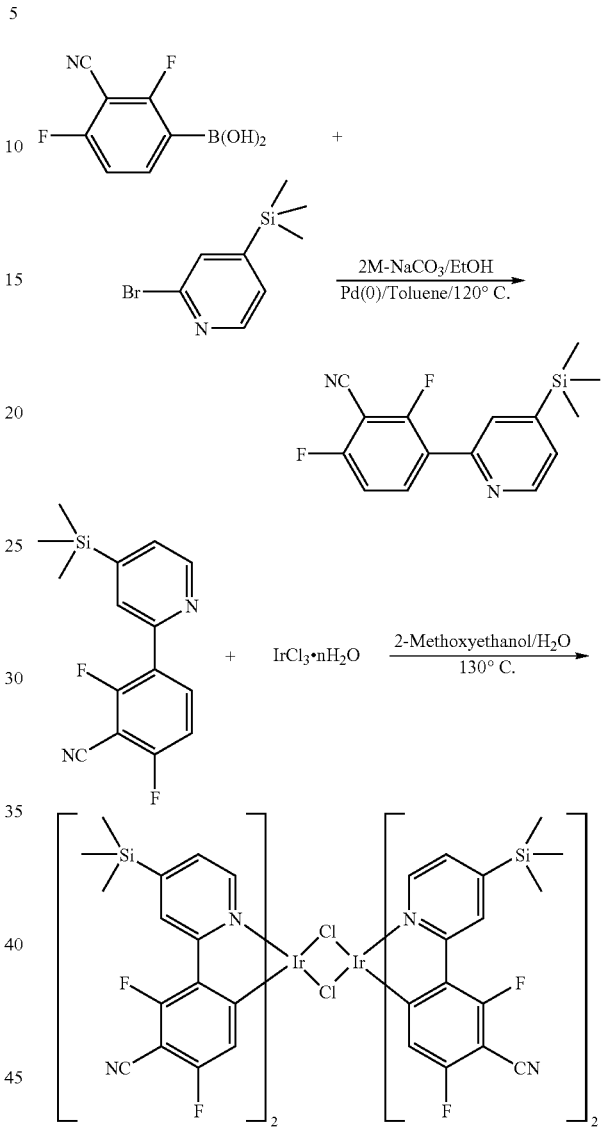

A 2-(2,4-difluoro-3-cyanophenyl)-trimethylsilylpyridine ($F_2$CNpTMSpy) ligand synthesized by general Suzuki coupling and $IrCl_3 \cdot nH_2O$ were used to prepare a $F_2$CNpTMSpy dimer as a light green powder. The preparation method was described in J. Am. Chem. Soc., 1984, 106, 6647-6653 which is incorporated herein by reference.

Reference Example 2

Synthesis of $F_2$CNppy Dimer

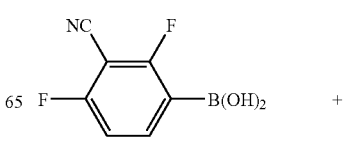

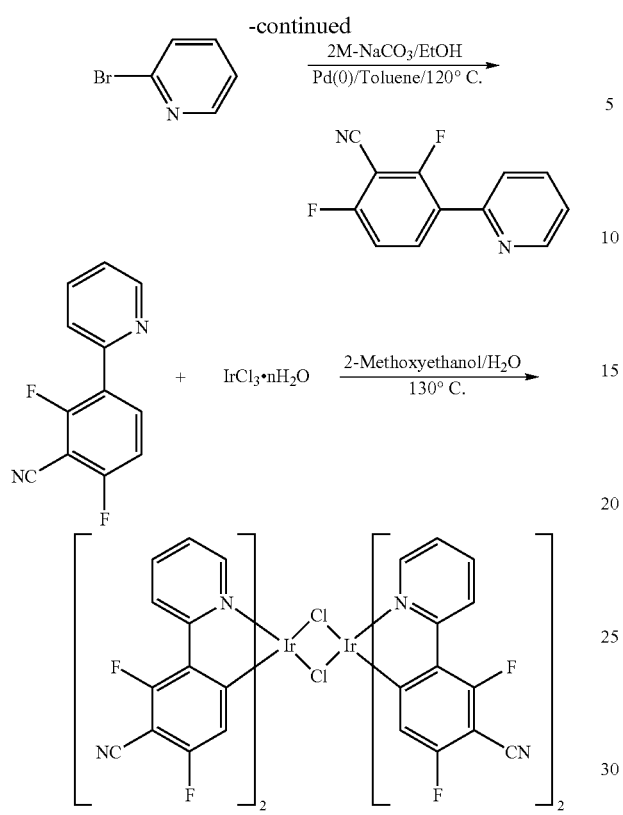

A 2-(2,4-difluoro-3-cyanophenyl)-pyridine (F₂CNppy) ligand synthesized by general Suzuki coupling and IrCl₃.nH₂O were used to prepare a F₂CNppy dimer as a light yellow powder. The preparation method was described in J. Am. Chem. Soc., 1984, 106, 6647-6653 which is incorporated herein by reference.

Example 1

Synthesis of Compound Represented by Formula 30 [(F₂CNpTMSpy)₂IrPIC]

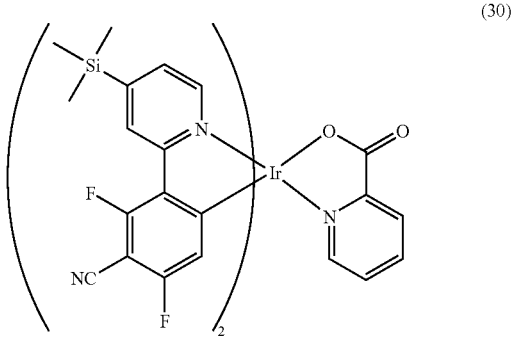

In a 100 mL 2-neck flask equipped with a thermometer, a magnetic stirrer, and a reflux condenser, 0.16 g (0.1 mmol) of [(F₂CNpTMSPy)₂IrCl]₂ prepared in the Reference Example 1 and 0.030 g (0.25 mmol) of pyridine-3-carboxylic acid were dissolved in THF under a nitrogen atmosphere and refluxed at 50° C. for 15 hours. After the reaction was completed, the reaction mixture was cooled to room temperature and the solvent was removed under vacuum. The remaining solids were dissolved in chloroform and filtered. The filtrate was purified using a column chromatography. A mixed solvent consisting of chloroform and methanol (10:1) was used as an eluent. A yellow product was obtained (yield 80%). The product was identified through ¹H-NMR spectroscopy and MS (FIG. 1A).

Example 2

Synthesis of Compound Represented by Formula 31 [(F₂CNpTMSpy)₂Iracac]

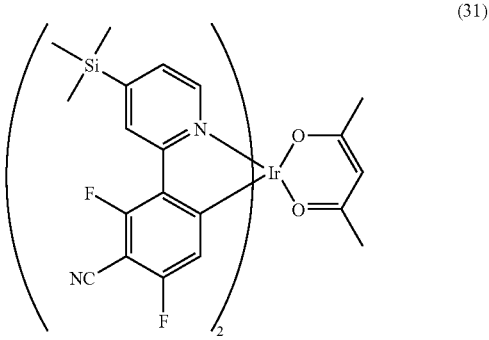

Figure 1B:
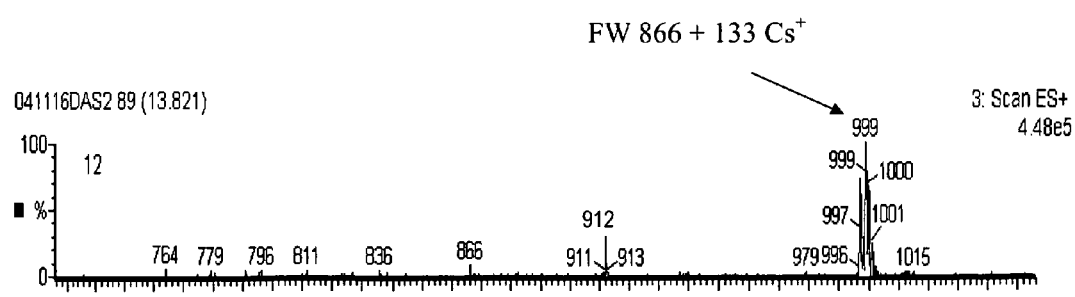

The title compound was prepared in the same manner as in Example 1, except that 0.025 g (0.25 mmol) of 2,4-pentanedione was used instead of pyridine-3-carboxylic acid. Instead of THF a mixture of THF and MeOH (4:1) were used as the solvents. 0.120 g of the product was obtained as a pure yellow solid (yield 80%). The product was identified through ¹H-NMR spectroscopy and MS (FIG. 1B).

Comparative Example 1

Synthesis of Compound Represented by Formula (32)[(F2CNppy)₂IrPIC]

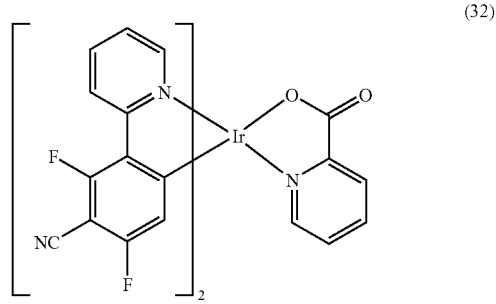

The title compound was prepared in the same manner as in Example 1, except that 0.131 g (0.1 mmol) of 2,4-difluoro-3-cyanophyenylpyridine (F₂CNppy) was used instead of 2,4-difluoro-3-cyanophenyltrimethylsilylpyridine (F₂CNpTMSpy). 0.118 g of the product was obtained as a pure yellow solid (yield 80%).

The obtained compounds were tested for emission characteristics in the following manners.

94 parts by weight of polymethylmethacrylate (PMMA) and 6 parts by weight of the compounds prepared in Examples 1 and 2 and Comparative Example 1 were dissolved in a solvent and spin-coated to be fabricated into a film. Then, the emission characteristics of the compounds in a film state were evaluated.

The maximum emission wavelength ($\lambda_{max}$), color coordinate (CIE), decomposition temperature, and HOMO level of the compounds prepared in Examples 1 and 2 and Comparative Example 1 are summarized in Table 1.

TABLE 1

| Compound | $\lambda_{max}$ | Color coordinate | Decomposition temperature | HOMO |
|---|---|---|---|---|
| Formula 30 (Example 1) | 465 | 0.14, 0.18 | 342 | 6.18 |
| Formula 31 (Example 2) | 475 | 0.14, 0.25 | 360 | 6.02 |
| Formula 32 (Comparative Example 1) | 458 | 0.14, 0.13 | — | — |

The compounds synthesized in Examples 1 and 2 and Comparative Example 1 were used to manufacture multilayered EL devices having an emission area of 9 mm² and the following structure:

Substrate/first electrode/hole transport layer/emission layer/hole blocking layer/electron transport layer/electron injection layer/second electrode=glass/ITO/PEDOT: PSS (40 nm)/PS 24%+mCP 72%+dopant 6% (40 nm)/BAlq (40 nm)LiF/Al. (ITO: Iridium tin oxide; PEDOT: (poly(3,4-ethylenedioxythiophene); PSS: polystyrenesulfonate; mCP1,3-N,N-dicarbazole-benzene; BAlq: aluminum(III)bis(2-methyl-8-quinolinato).sub.4-phenylphenolate.)

The devices were manufactured as described below.

PEDOT: PSS was deposited on a previously-washed ITO (indium-tin oxide) substrate to a thickness of 40 nm, and PS 24%, mCP 72%, and dopant 6% were coated thereon to a thickness of 40 nm. Next, BAlq was thermally deposited to form a 40 nm thick hole blocking layer and LiF was deposited to form a 2 nm thick electron transport layer. Finally, Al was coated to form a 200 nm thick anode.

The electroluminescence devices manufactured above were tested for maximum emission wavelength (λmax), color coordinate (CIE), luminescence efficiency ($\eta_A$), luminescence, lifespan and the like. The results are listed in Table 2.

TABLE 2

| Compound | $\lambda_{max}$ | CIE | $\eta_A$ | $\eta_{ex}$ | Maximum luminescence |
|---|---|---|---|---|---|
| Formula 30 (Example 1) | 472 | 0.17, 0.26 | 2.09 | 3.1 | 6272 |
| Formula 31 (Example 2) | 470 | 0.15, 0.30 | 2.83 | — | 7475 |
| Formula 32 (Comparative Example 1) | 458 | 0.17, 0.24 | 1.68 | — | 5605 |

Figure 2A:
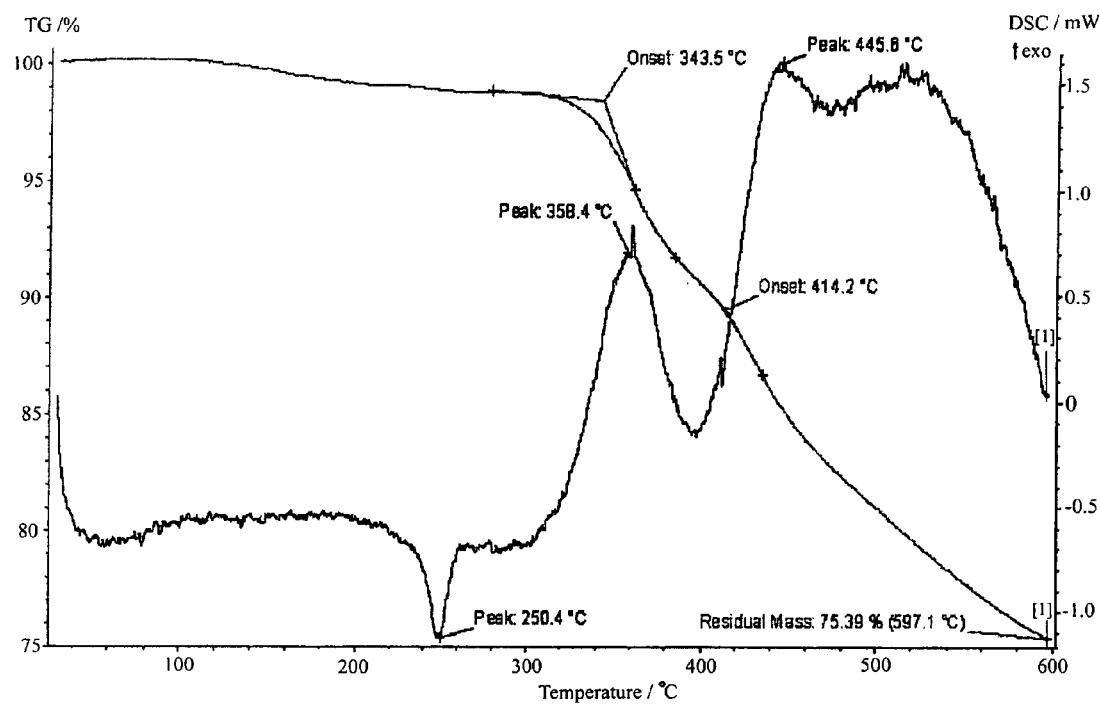
FIGS. 2A and 2B shows the thermogravimetric analysis (TGA) of the compounds prepared in the Examples 1 and 2 of the present invention, respectively.
Figure 2B:
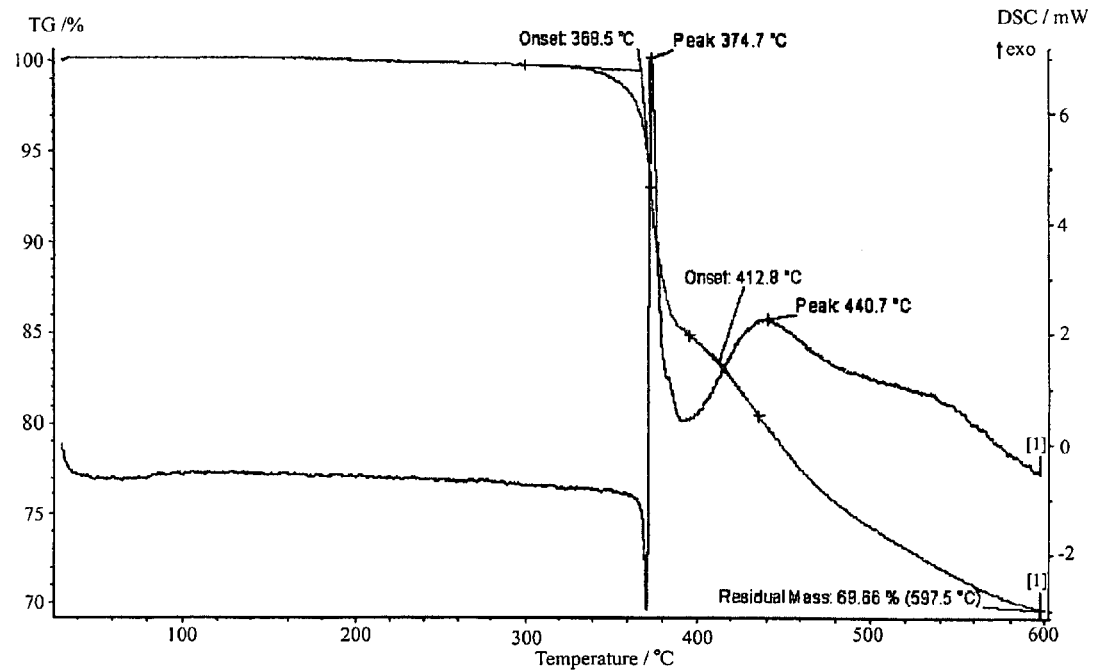
Figure 3:
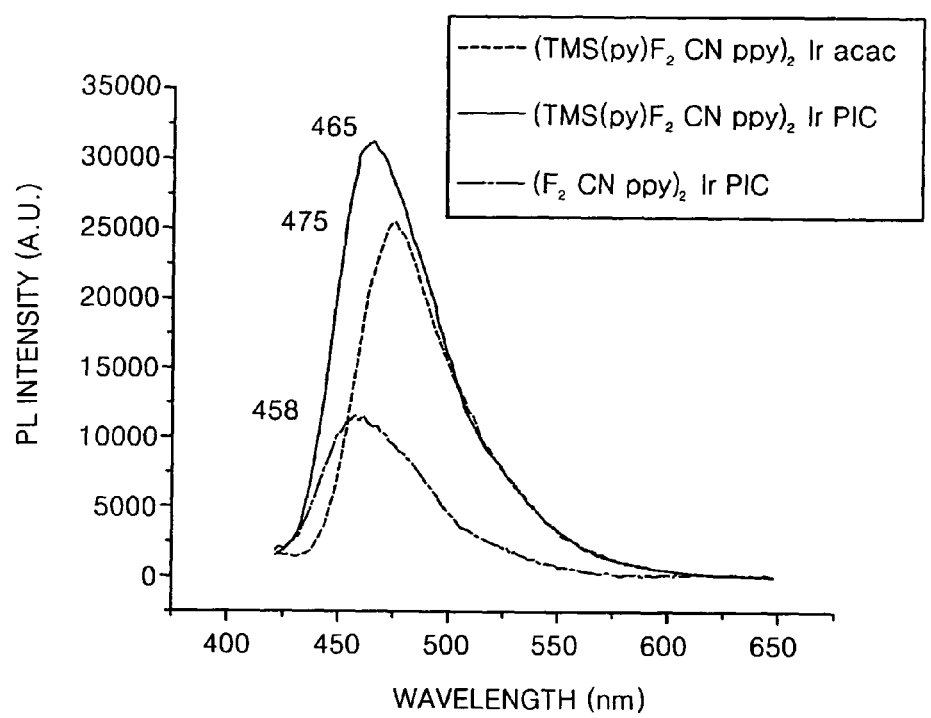
FIG. 3 is a photoluminescence (PL) spectrum of the compounds prepared in the Examples 1 and 2 and Comparative Example 1.
Figure 4:
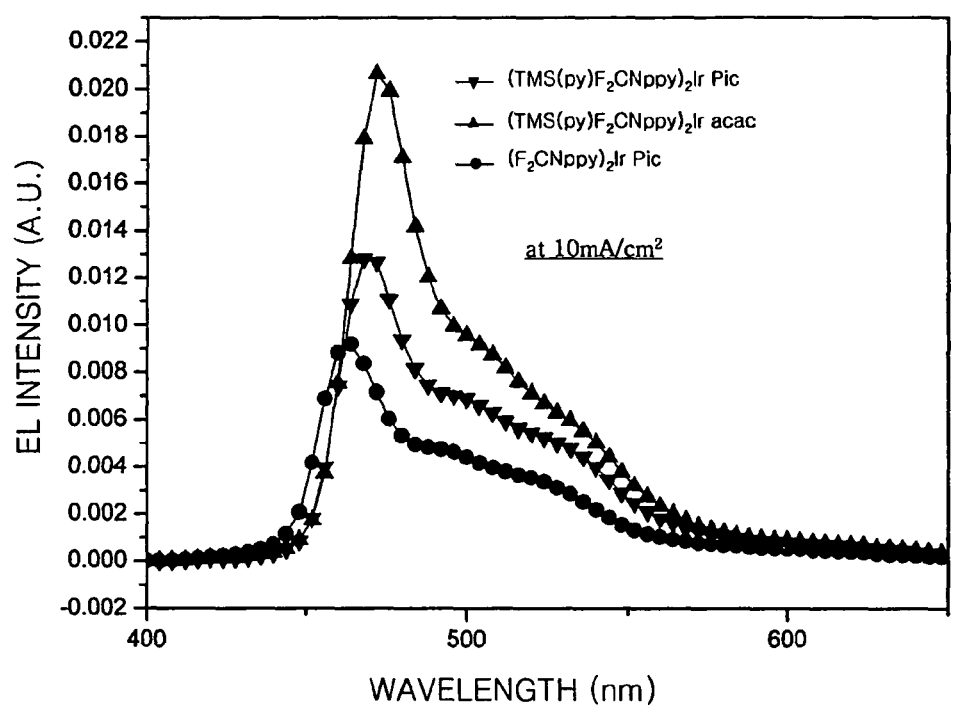
FIG. 4 is an electroluminescence (EL) spectrum of the compounds prepared in the Examples 1 and 2 and Comparative Example 1.

FIGS. 1A and 1B are mass spectra of the compounds prepared in Examples 1 and 2 of the present invention. FIGS. 2A and 2B are thermogravimetric analyzer (TGA) spectra of the compounds prepared in Examples 1 and 2 of the present invention. FIG. 3 is a photoluminescence (PL) spectrum in a film state of the compounds prepared in Examples 1 and 2 and Comparative Example 1. FIG. 4 is an electroluminescence (EL) spectrum of the compounds prepared in Examples 1 and 2 and Comparative Example 1.

Figure 5:
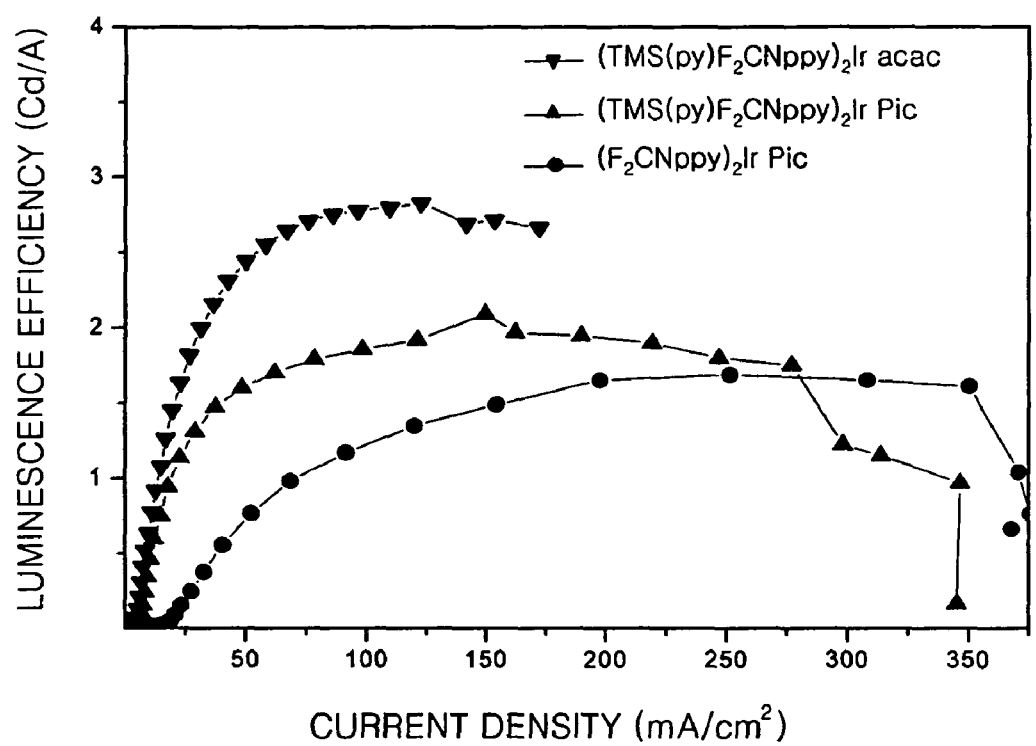
FIG. 5 is a graph illustrating the luminescence efficiency of the compounds of the Examples 1 and 2 and Comparative Example 1.
Figure 6A:
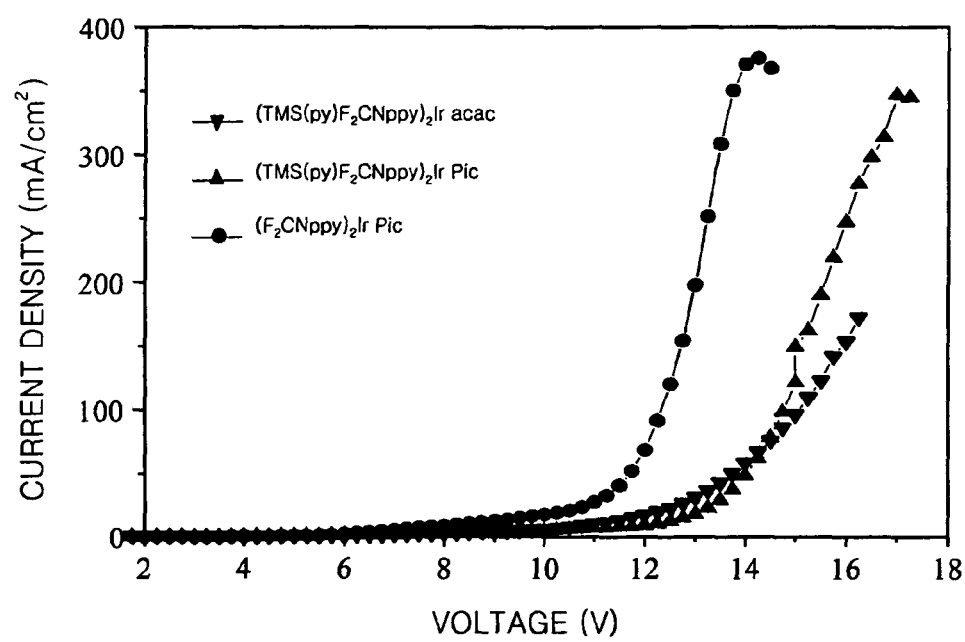
FIGS. 6A and 6B are graphs illustrating the current-voltage-luminescence (I-V-L) characteristics of the organic electroluminescence devices using the compounds prepared in the Examples 1 and 2 and Comparative Example 1.
Figure 6B:
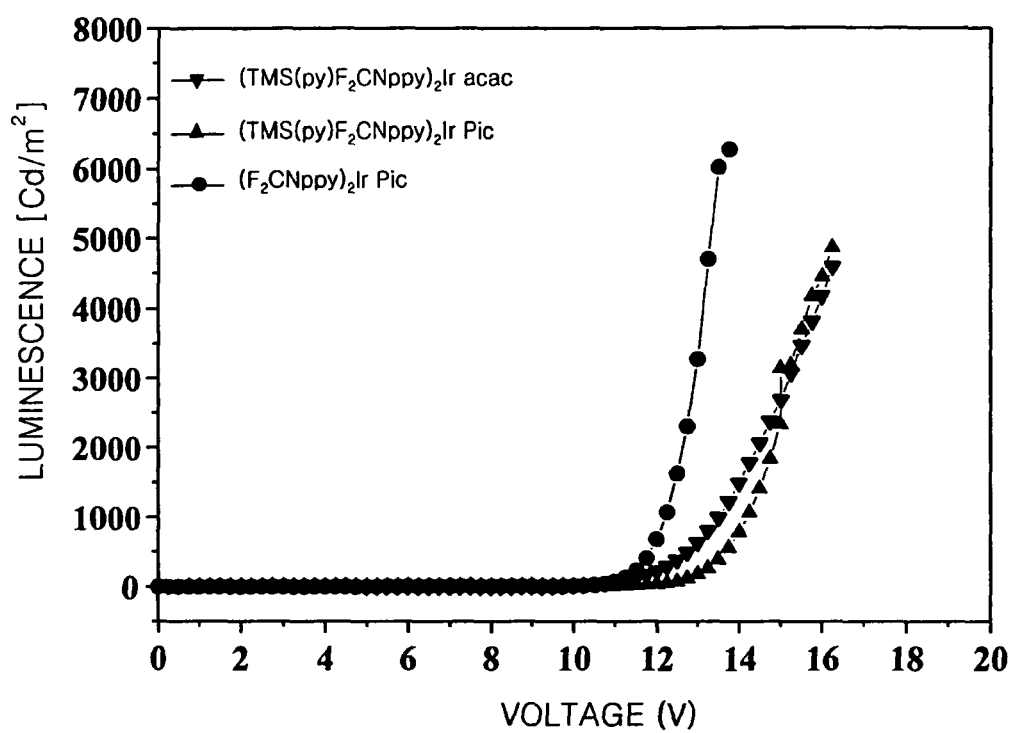

FIG. 5 is a graph illustrating luminescence efficiency of the compounds of Examples 1 and 2 and the Comparative Example 1 and FIGS. 6A and 6B are graphs illustrating current-voltage-luminescence (I-V-L) characteristics of organic electroluminescence devices using the compounds prepared in Examples 1 and 2 and Comparative Example 1. It can be seen from Table 2 that the compound of Example 1 had similar color coordinate to the compound of Comparative Example 1, but had about 20% higher efficiency than the compound of Comparative Example 1. In addition, as apparent from Table 1, the compound (acac) of Example 2 had a higher y value of color coordinate than the compound (picolinate) of Example 1, but had superior efficiency and heat stability to the compound of Example 1.

It can be seen from the above results that the silyl-substituted cyclometalated transition metal complex according to the present invention forms a dopant having good phospholuminescence and is suitable as blue phospholuminescent materials. Also, introduction of various main ligands enables a full color display of red, green and blue lights.

The silyl-substituted cyclometalated transition metal complex represented by Formula 1 can efficiently emit light of wavelengths from a blue range to a red range using triplet MLCT. The organometallic complex is suitably used for forming an organic layer of the organic electroluminescent device, and can emit light in a wavelength range of 400-650 nm. Also, it can induce white electroluminescence when combined with green or red luminescent materials.

While the present invention has been particularly shown and described with reference to preferred embodiments thereof, it will be understood by those of ordinary skill in the art that various changes in form and details may be made therein without departing from the spirit and scope of the present invention as defined by the following claims.

What is claimed is:

1. A silyl-substituted cyclometalated transition metal complex represented by Formula (1):

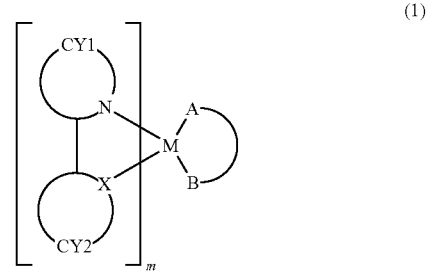

(1)

wherein M is a transition metal;
X is S, or O;
CY1 and CY2 are each an aromatic or aliphatic ring;
A^ is a monoanionic bidentate chelating ligand selected from the group consisting of groups represented by Formulae (24) through (29):

(24)

-continued (25)

(26)

(27)

wherein Y is C, or N, with the proviso that all of Ys are not N; and

R is each independently alkyl, arylalkyl, alkoxy, or aryloxy, in which each ring of arylalkyl or aryloxy may be substituted with halogen, $CF_3$, CN, silyl, alkyl, aryl, alkoxy, aryloxy, amino, or arylene;

at least one of CY1, CY2, and A^B has a silyl group represented by Formula $SiR^1R^2R^3$, in which $R^1$, $R^2$, and $R^3$ are each independently alkyl, aryl, alkyloxy, or aryloxy; and m is 1 or 2.

2. The silyl-substituted cyclometalated transition metal complex of claim 1, wherein the M is Ru, Rh, Os, Ir, Pt, or Au.

3. The silyl-substituted cyclometalated transition metal complex of claim 2, wherein the M is Ir.

4. The silyl-substituted cyclometalated transition metal complex of claim 1, wherein X is S.

5. A silyl-substituted cyclometalated transition metal complex represented by Formula (30) or Formula (31):

(30)

(31)

6. The silyl-substituted cyclometalated transition metal complex of claim 5, being a compound represented by Formula (30).

7. An organic electroluminescent device, comprising:
   a pair of electrodes; and
   an organic layer between the pair of electrodes, the organic layer comprising a silyl-substituted cyclometalated transition metal complex represented by Formula (1):

(1)

wherein M is a transition metal;

X is S, or O;

CY1 and CY2 are each an aromatic or aliphatic ring;

A^B is a monoanionic bidentate chelating ligand selected from the group consisting of groups represented by Formulae (24) through (29):

(24)

-continued

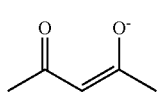 (25)

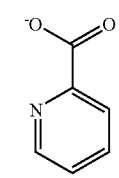 (26)

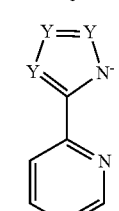 (27)

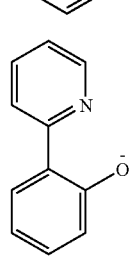 (28)

(29)

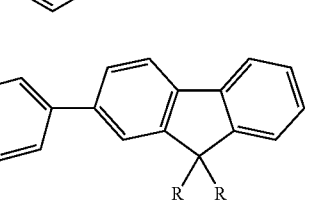

wherein Y is C, or N, with the proviso that all of Ys are not N; and

R is each independently alkyl, arylalkyl, alkoxy, or aryloxy, in which each ring of arylalkyl or aryloxy may be substituted with halogen, $CF_3$, CN, silyl, alkyl, aryl, alkoxy, aryloxy, amino, or arylene;

at least one of CY1, CY2, and A^B has a silyl group represented by formula $SiR^1R^2R^3$, in which $R^1$, $R^2$, and $R^3$ are each independently alkyl, aryl, alkyloxy, or aryloxy; and m is 1 or 2.

8. The organic electroluminescent device of claim 7, wherein the organic layer further comprises at least one selected from the group consisting of a high molecular weight host, a mixture of a high molecular weight host and a low molecular weight host, a low molecular weight host, and a non-luminous high molecular weight matrix.

9. The organic electroluminescent device of claim 7, wherein the organic layer further comprises a green electroluminescent material or a red electroluminescent material.

10. The organic electroluminescent device of claim 7, wherein a thickness of the organic layer is in a range of 30 nm to 100 nm.

11. The organic electroluminescent device of claim 7, wherein X is O.

12. The organic electroluminescent device of claim 7, wherein the organic layer is an emission layer.

13. The organic electroluminescent device of claim 12, wherein the silyl-substituted cyclometalated transition metal complex represented by Formula (1) is contained in an amount of about 1 to 30 parts by weight based on 100 parts by weight of the emission layer forming material.

14. An organic electroluminescent device, comprising:
a pair of electrodes; and
an organic layer between the pair of electrodes, the organic layer comprising a silyl-substituted cyclometalated transition metal complex selected from the group consisting of compounds represented by Formulae (30) and (31):

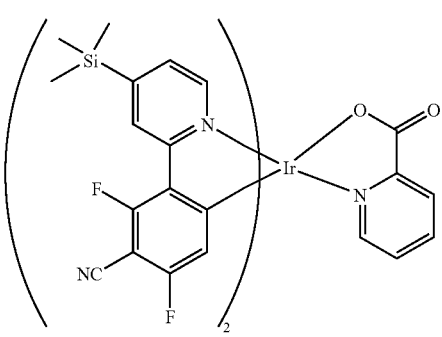 (30)

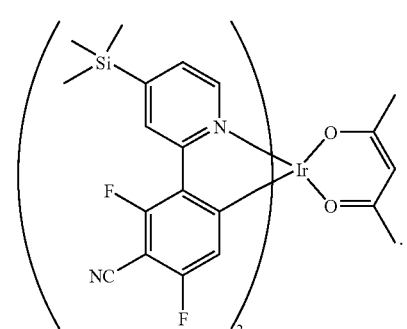 (31)

15. An organic electroluminescent device, comprising:
a pair of electrodes; and
an organic layer between the pair of electrodes, the organic layer comprising a silyl-substituted cyclometalated transition metal complex represented by Formula (1):

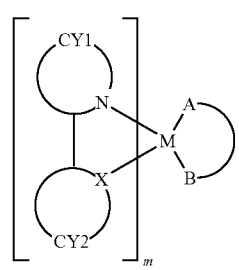 (1)

wherein M is a transition metal;

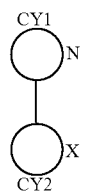
is a group selected from the group consisting of groups represented by Formulae (2) to (23):
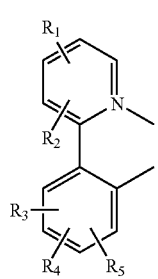 (2)
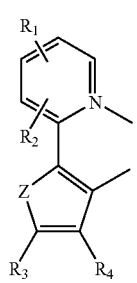 (3)
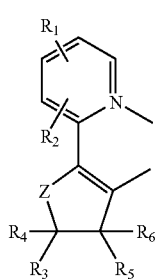 (4)
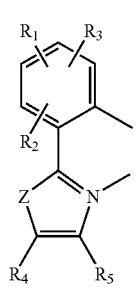 (5)
-continued
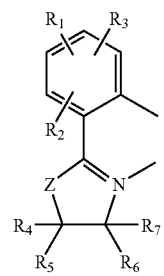 (6)
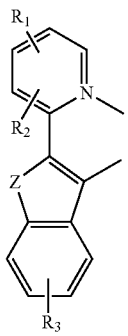 (7)
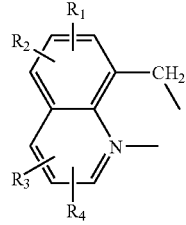 (8)
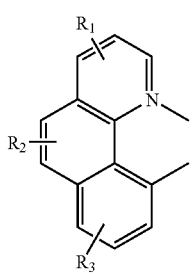 (9)
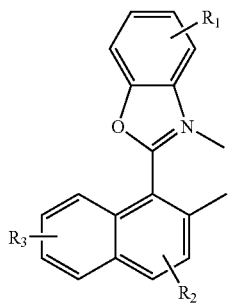 (10)

-continued
(11) 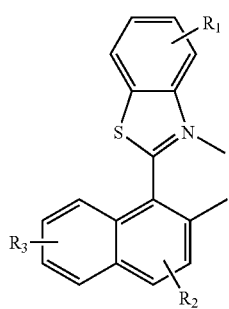
(12) 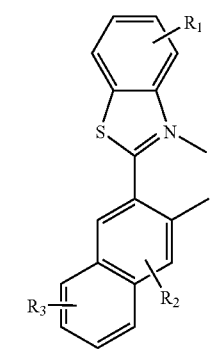
(13) 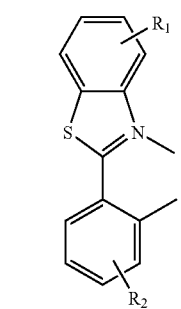
(14) 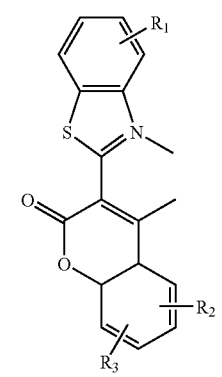
(15) 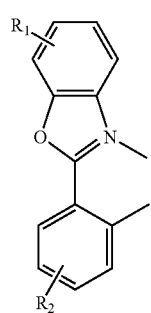
-continued
(16) 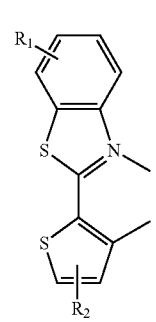
(17) 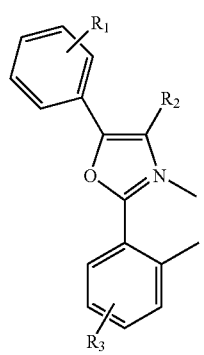
(18) 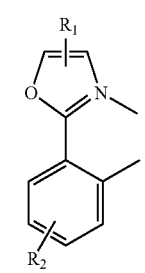
(19) 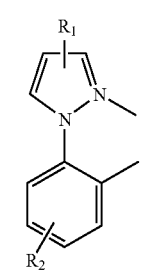
(20) 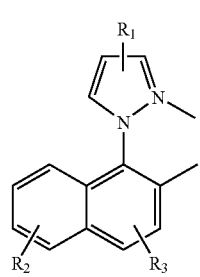

-continued (21)

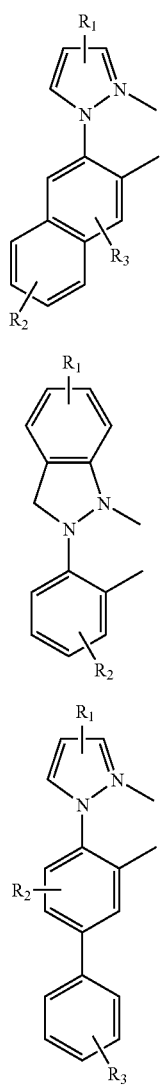

(22)

(23)

wherein Z is S, O, or NR$_8$, and R$_1$, R$_2$, R$_3$, R$_4$, R$_5$, R$_6$, R$_7$, and R$_8$ are each independently selected from the group consisting of hydrogen, halogen, CF$_3$, CN, silyl, alkyl, aryl, alkoxy, aryloxy, amino, and arylene; A︿B is selected from the group consisting of groups represented by Formulae (24) through (29) having a substituent of a silyl group represented by Formula SiR$^1$R$^2$R$^3$, in which R$^1$, R$^2$, and R$^3$ are each independently alkyl, aryl, alkyloxy, or aryloxy:

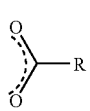

(24)

-continued

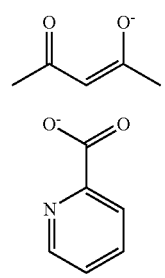

(25)

(26)

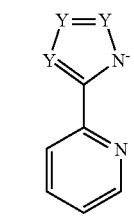

(27)

(28)

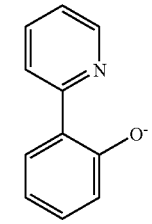

(29)

wherein Y is C, or N, with the proviso that all of Ys are not N, and R is each alkyl, arylalkyl, alkoxy, or aryloxy, in which each ring of arylalkyl or aryloxy may be substituted with halogen, CF$_3$, CN, silyl, alkyl, aryl, alkoxy, aryloxy, amino, or arylene;

at least one of CY1, CY2, and A︿b has a silyl group represented by Formula SiR$^1$R$^2$R$^3$, in which R$^1$, R$^2$, and R$^3$ are each independently alkyl, aryl, alkyloxy, or aryloxy; and m is 1 or 2.

16. The organic electroluminescent device of claim 15, wherein the silyl-substituted cyclometalated transition metal complex represented by formula (1) is contained in an amount of about 1 to 30 parts by weight based on 100 parts by weight of the organic layer forming material, and a thickness of the organic layer is in a range of 30 nm to 100 nm.

17. The organic electroluminescent device of claim 15, wherein the organic layer is an emission layer.

* * * * *